US00PP34129P2

(12) United States Plant Patent
Hartman et al.

(10) Patent No.: US PP34,129 P2
(45) Date of Patent: Apr. 12, 2022

(54) ***ALOCASIA* PLANT NAMED 'AP091520'**

(50) Latin Name: *Alocasia hybrida*
Varietal Denomination: AP091520

(71) Applicant: CLASSIC CALADIUMS LLC, Avon Park, FL (US)

(72) Inventors: Robert Dale Hartman, Lake Placid, FL (US); Joseph Clayton Wallace, Jr., Sebring, FL (US)

(73) Assignee: Classic Caladiums LLC, Avon Park, FL (US)

( * ) Notice: Subject to any disclaimer, the term of this patent is extended or adjusted under 35 U.S.C. 154(b) by 0 days.

(21) Appl. No.: 17/462,454

(22) Filed: Aug. 31, 2021

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10
See application file for complete search history.

*Primary Examiner* — Anne Marie Grunberg
(74) *Attorney, Agent, or Firm* — C. Anne Whealy

(57) ABSTRACT

A new and distinct cultivar of *Alocasia* plant named 'AP091520', characterized by its tall and upright plant habit that becomes outwardly arching with development; vigorous growth habit and rapid growth rate; glossy green-colored and undulate leaves that are initially held vertically becoming more horizontal with development; and green-colored leaf petioles that are initially erect and arch outwardly with development.

3 Drawing Sheets

Figure 1:
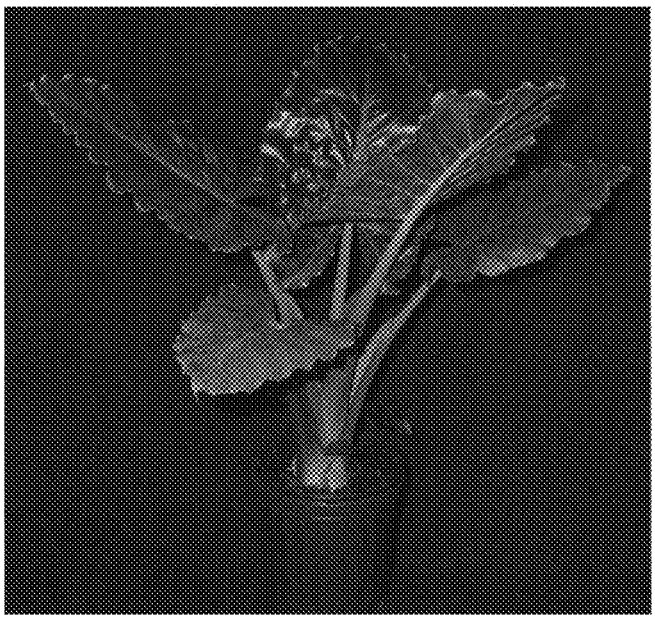

Botanical designation: *Alocasia hybrida.*
Cultivar denomination: 'AP091520'.

STATEMENT REGARDING PRIOR DISCLOSURES BY INVENTOR/APPLICANT

The Inventors and Applicant asserts that no publications nor advertisements relating to sales, offers for sale or public distribution occurred more than one year prior to the effective filing date of this application. Any information about the claimed plant would have been obtained from a direct or indirect disclosure from the Inventors and/or Applicant. Inventors and Applicant hereby claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Alocasia* plant, botanically known as *Alocasia hybrida*, commercially referred to as Elephant Ear *Alocasia* and hereinafter referred to by the name 'AP091520'.

The new *Alocasia* plant is a naturally-occurring whole plant mutation of *Alocasia hybrida* 'Portora', not patented. The new *Alocasia* plant was discovered and selected by the Inventors as a single plant from within a population of plants of 'Portora' in a controlled outdoor nursery environment in Zolfo Springs, Fla. on Sep. 15, 2020.

Asexual reproduction of the new *Alocasia* plant by "chipping" the rhizomes (cutting the rhizomes into segments with each segment containing an axillary bud and cortical tissue) in a controlled outdoor nursery environment in Zolfo Springs, Fla. since Dec. 4, 2020 has shown that the unique features of this new *Alocasia* plant are stable and reproduced true to type in successive generations of asexual reproduction.

SUMMARY OF THE INVENTION

Plants of the new *Alocasia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'AP091520'. These characteristics in combination distinguish 'AP091520' as a new and distinct *Alocasia* plant:

1. Tall and upright plant habit that becomes outwardly arching with development.
2. Vigorous growth habit and rapid growth rate.
3. Glossy green-colored and undulate leaves that are initially held vertically becoming more horizontal with development.
4. Green-colored leaf petioles that are initially erect and arch outwardly with development.

Plants of the new *Alocasia* differ primarily from plants of the mutation parent, 'Portora', in the following characteristics:

1. Plants of the new *Alocasia* are more outwardly arching than and not as upright as plants of 'Portora'.
2. Leaves of plants of the new *Alocasia* are glossier in luster than leaves of plants of 'Portora'.
3. Leaves of plants of the new *Alocasia* are more undulate than leaves of plants of 'Portora'.

4. Leaf petioles of plants of the new *Alocasia* are green in color whereas leaf petioles of plants of 'Portora' are purple in color variably flushed with greyed purple.

Plants of the new *Alocasia* can be compared to plants of *Alocasia hybrida* 'Low Rider', not patented. In side-by-side comparisons, plants of the new *Alocasia* differ primarily from plants of 'Low Rider' in the following characteristics:

1. Plants of the new *Alocasia* are taller than plants of 'Low Rider'.
2. Plants of the new *Alocasia* are not as freely branching as plants of 'Low Rider'.
3. Leaf petioles of plants of the new *Alocasia* are green in color whereas leaf petioles of plants of 'Low Rider' are purple in color variably flushed with greyed purple.

Plants of the new *Alocasia* can also be compared to plants of *Alocasia hybrida* 'Calidora', not patented. In side-by-side comparisons, plants of the new *Alocasia* differ primarily from plants of 'Calidora' in the following characteristics:

1. Plants of the new *Alocasia* are not as freely branching as plants of 'Calidora'.
2. Leaves of plants of the new *Alocasia* are more undulate than leaves of plants of 'Calidora'.

BRIEF DESCRIPTION OF THE PHOTOGRAPHS

The accompanying photographs illustrate the overall appearance of the new *Alocasia* plant showing the colors as true as it is reasonably possible to obtain in colored reproductions of this type. Colors in the photographs may differ slightly from the color values cited in the detailed botanical description which accurately describe the colors of the new *Alocasia* plant.

The photograph on the first sheet (FIG. 1) is a side perspective view of a typical plant of 'AP091520' grown in a container.

Figure 2:
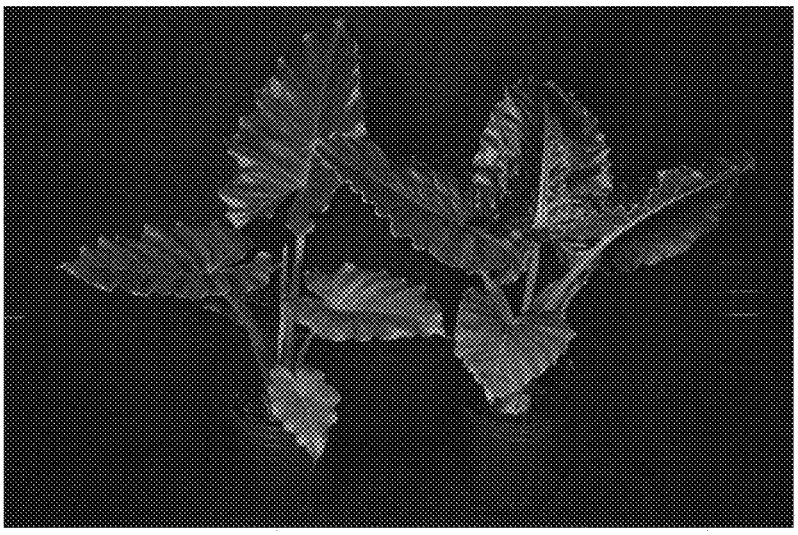

The photograph at the top of the second sheet (FIG. 2) is side perspective view of typical plants of the mutation parent, 'Portora' (left) and 'AP091520' (right).

Figure 3:
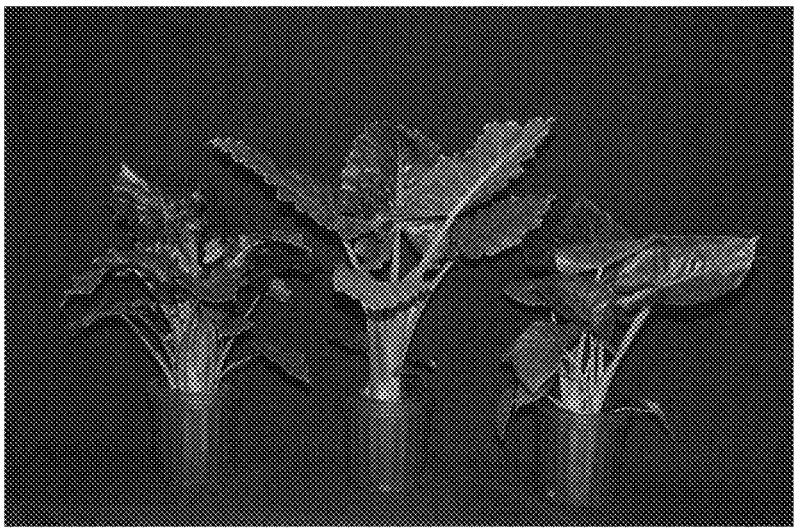

The photograph at the bottom of the second sheet (FIG. 3) is side perspective view of typical plants of 'Low Rider' (left), 'AP091520' (center) and 'Calidora' (right).

Figure 4:
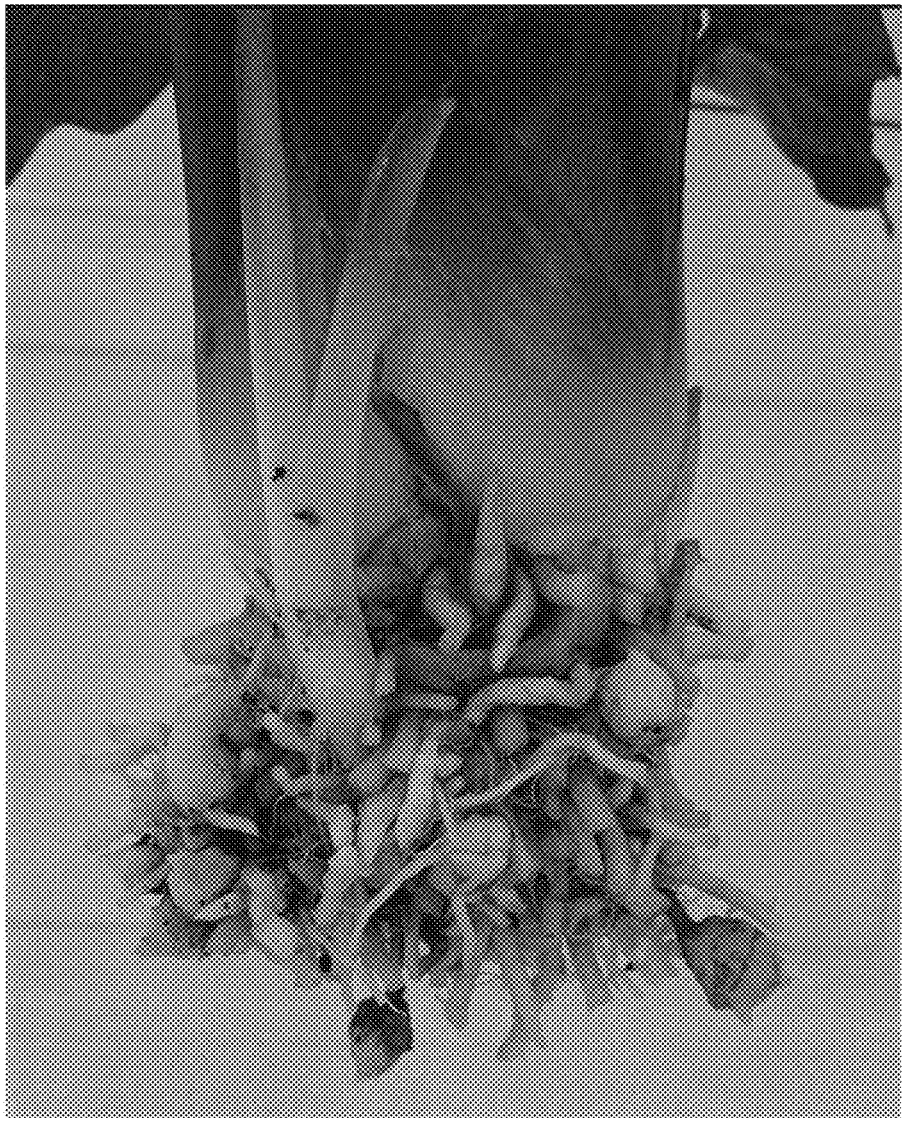

The photograph on the third sheet (FIG. 4) is a close-up view of the base of a typical plant 'AP091520' showing the roots and cormels.

DETAILED BOTANICAL DESCRIPTION

The aforementioned photographs and following observations and measurements describe plants grown in 25-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 750 μmol. During the production of the outdoor nursery-grown plants, day temperatures ranged from about 29° C. to 35° C., night temperatures ranged from about 23° C. to 26° C. and full sunlight conditions. Plants grown in the shade house were 13 weeks old and plants grown in the outdoor nursery were seven months old when the photographs and the detailed description were taken. In the following description, color references are made to The Royal Horticultural Society Colour Chart, 2015 Edition, except where general terms of ordinary dictionary significance are used.

Botanical classification: *Alocasia hybrida* 'AP091520'.

Parentage: Naturally-occurring whole plant mutation of *Alocasia hybrida* 'Portora', not patented.

Propagation:

*Type*.—By "chipping" the rhizomes.

*Time to initiate roots, summer*.—About seven to ten days at temperatures about 32° C.

*Time to initiate roots, winter*.—About two to three weeks at temperatures about 24° C.

*Primary rhizome description*.—Appearance: Thick, fibrous and somewhat starchy; rigid. Length: About 10.5 cm. Diameter: About 6.9 cm. Texture and luster: Initially, smooth and glossy; with maturity, becoming tough and somewhat woody. Color, outside: When harvested, close to 145D; when dry, close to 200A; axillary buds, close to 147D. Color, inside: Close to NN155D.

*Secondary rhizome description*.—Length: About 2 cm to 4.5 cm. Diameter: About 3 mm to 4 mm. Texture and luster: Smooth and glossy. Color, outside and inside: Close to NN155D.

*Cormel description*.—Length: About 1 cm to 2.4 cm. Diameter: About 5 mm to 15 mm. Texture and luster, outside: Smooth; matte. Texture and luster, inside: Smooth, starchy, somewhat brittle; matte. Color, outside: Close to 159D and 155D. Color, inside: Close to NN155D.

*Root description*.—Thick, fleshy roots with many fine lateral branches; color, close NN155C.

*Rooting habit*.—Dense.

Plant description:

*Plant type*.—Herbaceous perennial; suitable as a potted plant in containers 15-cm to 25-cm and suitable as a landscape plant in full sun or shaded areas.

*Plant and growth habit*.—Tall and upright plant habit becoming outwardly arching with development; vigorous growth habit and rapid growth rate; potted plants in 20 to 25-cm containers finish in saleable form in about 12 to 14 weeks after planting; leaf petioles and leaves arise from one or more growing points on rhizomes; leaf petioles initially upright and arching outwardly with development; undulate leaves initially held vertically becoming more horizontal with development.

*Plant height, from soil level to top of foliar plane*.—About 54 cm to 70 cm.

*Plant diameter or spread*.—About 70 cm to 87 cm.

*Number of leaves per plant*.—About four to six leaves develop per primary shoot and about one to two leaves on young axillary shoots.

*Cataphylls*.—Length: About 2 cm to 9 cm. Width: About 1.2 cm to 2 cm. Shape: Lance-shaped or strap-like. Apex: Cuspidate. Base: Sheathing the stein. Texture and luster: Smooth, glabrous; glossy. Color, inner and outer surfaces: Close to NN155C and 143D; color becoming closer to 199C with subsequent development.

Leaf description:

*Arrangement*.—Alternate; simple; initially held vertically becoming more horizontal with development.

*Length, flattened*.—About 35 cm to 49 cm.

*Width, flattened*.—About 22 cm to 30 cm.

*Shape*.—Ovate to cordate.

*Apex*.—When developing, acuminate, becoming cuspidate to apiculate with development.

*Base*.—Sagittate.

*Margin*.—Entire; undulate.

*Texture and luster, upper surface*.—Slightly rugose, glabrous; flexible; glossy.

*Texture and luster, lower surface*.—Smooth, glabrous; glossy to satiny.

*Venation pattern*.—Pinnate; eucamptodromous.

*Color*.—Developing leaves, upper surface: Interveinal areas: Close to 137C tinged with close to 137A. Margins: Close to 138A to 138B tinged with close to 144B. Basal notch: Close to 138A to 138B. Midvein: Close to 137C. Lateral venation: Close to 137B to 137C. Developing leaves, lower surface: Interveinal areas: Close to 138B. Margins: Close to 138B. Basal notch: Close to 138B. Midvein and lateral venation: Close to 145B to 145C. Fully developed leaves, upper surface: Interveinal areas: Close to 137A and NN137A. Margins: Close to 137A and NN137A. Basal notch: Close to 137A and NN137A. Midvein and lateral venation: Close to 137B to 137C. Fully developed leaves, lower surface: Interveinal areas: Close to 137C. Margins: Close to 137C Basal notch: Close to 137C. Midvein: Close to 145B to 145C. Lateral venation: Close to 145C.

*Petioles*.—Aspect: Initially upright and straight and outwardly arching with development; flexible. Length: About 36 cm to 49 cm. Diameter, distally: About 1 cm to 1.5 cm. Diameter, proximally: About 4.5 cm to 5 cm. Texture and luster: Smooth, glabrous; matte. Color: Close to 137C; just below the leaf junction, close to 137B to 137C. Wing length: About 27 cm to 32 cm. Wing diameter: About 2 cm to 2.2 cm Wing texture and luster, inner surface: Smooth, glabrous; glossy. Wing texture and luster, outer surface: Smooth, glabrous; matte. Wing color, inner surface: Close to 139D with venation, close to 139C. Wing color, outer surface: Close to 137C.

Inflorescence description: To date, inflorescence initiation and development has not been observed on plants of the new *Alocasia*.

Pathogen tolerance: Plants of the new *Alocasia* have been observed to have average tolerance to *Pythium* Root Rot and above average tolerance to *Xanthomonas* Leaf Spot. Plants of the new *Alocasia* have not been observed to have tolerance/resistance to other pathogens common to *Alocasia* plants.

Temperature tolerance: Plants of the new *Alocasia* have been observed to tolerate temperatures ranging from about 7° C. to about 40° C. and are suitable for USDA Hardiness Zones 7b to 10b.

It is claimed:

1. A new and distinct *Alocasia* plant named 'AP091520' as illustrated and described.

* * * * *